United States Patent
Braun et al.

(10) Patent No.: US 9,636,077 B2
(45) Date of Patent: May 2, 2017

(54) METHOD AND SYSTEM FOR THE AUTOMATIC SELECTION OF A SCANNING PROTOCOL

(71) Applicant: Siemens Aktiengesellschaft, Munich (DE)

(72) Inventors: Christoph Braun, Rosenheim (DE); Dieter Böing, Forchheim (DE); Christiane Koch, Eggolsheim (DE); Robert Lapp, Nuremberg (DE); Michael Scheuering, Nuremberg (DE); Martin Sedlmair, Zirndorf (DE); Grzegorz Soza, Heroldsberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 127 days.

(21) Appl. No.: 14/487,265

(22) Filed: Sep. 16, 2014

(65) Prior Publication Data

US 2015/0085971 A1    Mar. 26, 2015

(30) Foreign Application Priority Data

Sep. 25, 2013   (DE) .................. 10 2013 219 249

(51) Int. Cl.
*A61B 6/03* (2006.01)
*A61B 6/00* (2006.01)
(Continued)

(52) U.S. Cl.
CPC .............. *A61B 6/545* (2013.01); *A61B 6/032* (2013.01); *A61B 6/0407* (2013.01); *A61B 6/463* (2013.01);
(Continued)

(58) Field of Classification Search
CPC .......... A61B 6/032; A61B 6/46; A61B 6/461; A61B 6/465; A61B 6/5294; A61B 6/54; A61B 6/541; A61B 6/542; A61B 6/545
(Continued)

(56) References Cited

U.S. PATENT DOCUMENTS

| | | | | |
|---|---|---|---|---|
| 5,400,378 A | * | 3/1995 | Toth ................. | A61B 6/032 378/108 |
| 5,450,462 A | * | 9/1995 | Toth ................. | A61B 6/032 378/108 |

(Continued)

FOREIGN PATENT DOCUMENTS

| | | |
|---|---|---|
| CN | 101004764 A | 7/2007 |
| CN | 101010039 A | 8/2007 |

(Continued)

OTHER PUBLICATIONS

Office Action dated Apr. 25, 2016 in Chinese Patent Application No. 2014104957002.

*Primary Examiner* — Allen C. Ho
(74) *Attorney, Agent, or Firm* — Harness, Dickey & Pierce, PLC

(57) ABSTRACT

A method is disclosed for automatically selecting a scanning protocol for a tomographic recording of an X-ray image of a patient in that at least one patient-specific value is retrieved in the internal memory of a first computer. The patient-specific value can in particular be a measure of the anticipated X-ray absorption by the patient. The method includes automatically comparing the patient-specific value with retrievably stored reference values, wherein one scanning protocol can be associated with each reference value. Finally, a scanning protocol is automatically selected by way of the first computer using the comparison. Selection is simplified by automation of selection of the scanning protocol since no manual selection of the scanning protocol has (Continued)

to be made. Automatic selection of a suitable scanning protocol is also quicker than a manual selection.

16 Claims, 2 Drawing Sheets

(51) Int. Cl.
*A61B 6/04* (2006.01)
*G01G 19/44* (2006.01)

(52) U.S. Cl.
CPC ............ *A61B 6/465* (2013.01); *A61B 6/5294* (2013.01); *A61B 6/54* (2013.01); *A61B 6/542* (2013.01); *A61B 6/544* (2013.01); *G01G 19/445* (2013.01)

(58) Field of Classification Search
USPC .............................. 378/8, 16, 98.7, 108–110
See application file for complete search history.

(56) References Cited

U.S. PATENT DOCUMENTS

| | | | | |
|---|---|---|---|---|
| 5,485,494 A * | 1/1996 | Williams | ............... | A61B 6/032 378/110 |
| 5,822,393 A * | 10/1998 | Popescu | ................. | A61B 6/032 378/108 |
| 5,867,555 A * | 2/1999 | Popescu | ................. | A61B 6/032 378/16 |
| 5,949,811 A * | 9/1999 | Baba | .................... | A61B 6/4225 378/108 |
| 6,094,468 A * | 7/2000 | Wilting | .................. | A61B 6/032 378/16 |
| 6,208,710 B1 * | 3/2001 | Nagai | ...................... | A61B 6/00 378/108 |
| 6,233,310 B1 * | 5/2001 | Relihan | .................... | H05G 1/46 378/108 |
| 6,259,767 B1 * | 7/2001 | Neumann | ................. | A61B 6/06 378/110 |
| 6,292,537 B1 * | 9/2001 | Zimmermann | ........ | A61B 6/542 378/108 |
| 6,333,965 B1 * | 12/2001 | Van Berkel | .............. | H05G 1/36 378/110 |
| 6,385,280 B1 * | 5/2002 | Bittl | ........................ | A61B 6/032 378/106 |
| 6,404,844 B1 * | 6/2002 | Horiuchi | ................. | A61B 6/032 378/16 |
| 6,490,337 B1 * | 12/2002 | Nagaoka | ................. | A61B 6/032 378/16 |
| 6,507,639 B1 * | 1/2003 | Popescu | ................. | A61B 6/032 378/108 |
| 6,754,301 B2 * | 6/2004 | Horiuchi | ................. | A61B 6/032 378/16 |
| 6,904,127 B2 * | 6/2005 | Toth | ....................... | A61B 6/032 378/108 |
| 7,054,412 B2 * | 5/2006 | Scheuering | ............ | A61B 6/589 378/108 |
| 7,103,139 B2 * | 9/2006 | Nagaoka | ................ | A61B 6/032 378/16 |
| 7,110,494 B2 * | 9/2006 | Groh | ..................... | A61B 5/4872 378/95 |
| 7,116,756 B2 * | 10/2006 | Klingenbeck-Regn | | A61B 5/1072 378/95 |
| 7,542,792 B2 * | 6/2009 | Wollenweber | ......... | A61B 6/032 250/370.08 |
| 7,620,142 B1 * | 11/2009 | Toth | ........................ | A61B 6/032 378/108 |
| 7,636,416 B2 * | 12/2009 | Miyazaki | ............... | A61B 6/542 378/108 |
| 7,639,776 B2 * | 12/2009 | Gohno | ................... | A61B 6/032 378/109 |
| 7,684,597 B2 * | 3/2010 | Kawano | .................. | G06T 5/009 378/16 |
| 7,720,198 B2 * | 5/2010 | Schliermann | ............ | A61B 6/08 378/108 |
| 7,778,381 B2 * | 8/2010 | Nishide | .................. | A61B 6/032 378/109 |
| 7,983,457 B2 * | 7/2011 | Toth | ........................ | A61B 6/032 378/16 |
| 8,000,510 B2 * | 8/2011 | Boeing | .................. | A61B 6/482 250/370.08 |
| 8,031,831 B2 * | 10/2011 | Zou | ......................... | A61B 6/032 378/108 |
| 8,204,290 B2 * | 6/2012 | Haras | ..................... | A61B 6/032 382/131 |
| 8,654,918 B2 * | 2/2014 | Eusemann | ............ | A61B 6/405 378/111 |
| 8,705,819 B2 * | 4/2014 | Carlsen | .................. | A61B 6/032 382/128 |
| 9,101,326 B2 * | 8/2015 | Tsai | ........................ | A61B 6/06 |
| 2005/0031080 A1 | 2/2005 | Klingenbeck-Regn et al. | | |
| 2005/0267348 A1 | 12/2005 | Wollenweber et al. | | |
| 2007/0238990 A1 | 10/2007 | Haras et al. | | |
| 2008/0101538 A1 | 5/2008 | Schliermann | | |
| 2009/0262892 A1 | 10/2009 | Haras | | |
| 2010/0040268 A1 | 2/2010 | Boeing et al. | | |
| 2010/0183206 A1 | 7/2010 | Carlsen et al. | | |
| 2011/0317806 A1 | 12/2011 | Eusemann et al. | | |

FOREIGN PATENT DOCUMENTS

| | | |
|---|---|---|
| CN | 101084839 A | 12/2007 |
| CN | 101686825 A | 3/2010 |
| CN | 102327124 A | 1/2012 |
| DE | 10333295 A1 | 2/2005 |
| DE | 102004042790 A1 | 3/2006 |
| DE | 102008014737 A1 | 10/2009 |
| DE | 102008037347 A1 | 2/2010 |
| DE | 102006001090 B4 | 11/2011 |
| DE | 102010041176 A1 | 12/2011 |
| JP | 6209928 A | 8/1994 |

\* cited by examiner

METHOD AND SYSTEM FOR THE AUTOMATIC SELECTION OF A SCANNING PROTOCOL

PRIORITY STATEMENT

The present application hereby claims priority under 35 U.S.C. §119 to German patent application number DE 102013 219249.5 filed Sep. 25, 2013, the entire contents of which are hereby incorporated herein by reference.

FIELD

At least one embodiment of the invention generally relates to a method and to a system for the automatic selection of a scanning protocol. At least one embodiment of the invention also generally relates to a computer program product and to an imaging system.

BACKGROUND

X-ray computed tomography is an imaging method which is primarily used for medical diagnosis and for material analysis. In X-ray computed tomography an X-ray emitter and an X-ray detector that cooperates with the X-ray emitter rotate about an object to be examined. Images are taken at various angular positions of X-ray emitter and X-ray detector, wherein the object to be examined can be moved along the axis of rotation. The individual images are each a projection of the object to be examined. At the end of the series of images, which is also called a "scan", the projections are processed in such a way that a three-dimensional, tomographic X-ray image is produced. Therefore carrying out a series of images will also be called a tomographic recording below. The quality of the resulting X-ray image is significantly influenced by the choice of scanning protocol. A scanning protocol includes values for parameters which determine the exact progress of the tomographic recording of an X-ray image.

A scanning protocol can also include values for parameters which influence the subsequent reconstruction of an X-ray image. The parameters can be by way of example intensity values of the X-ray radiation. Such intensity values can be modulated so as to be dependent on the projection angle in particular. The intensity values are specifically achieved by way of control of the X-ray emitter, i.e. by way of example by control of the current or voltage of an X-ray tube. The parameters of the scanning protocol can also include settings for filters or screens. In the medical environment the selection of a suitable scanning protocol is important in order to avoid unnecessary exposure of the patient to radiation as well as for the quality of the resulting image. If X-ray images of patients which absorb X-ray radiation to a particularly high or low degree are to be made, an existing scanning protocol must either be modified or a new scanning protocol which is suitable for such a case must be created. If more and more scanning protocols are created and retrievably stored, it becomes increasingly more laborious for the user of an X-ray tomograph to select a suitable scanning protocol from the large number of stored scanning protocols.

An operating method for an imaging device for improved selection of a contrast medium protocol is known from DE 10 2006 001 090 B4. A stored contrast medium protocol is selected from a database in which parameters of a contrast medium administration are stored. At least one linked scanning protocol relating to the selected contrast medium protocol is also identified in the database using a stored linkage parameter associated with the contrast medium protocol. The, or any, protocol identified in this way is then output as the scanning protocol associated with the selected contrast medium protocol.

SUMMARY

At least one embodiment of the invention simplifies and improves the selection of a scanning protocol for the tomographic recording of an X-ray image.

A method, a computer program product and a system are disclosed.

Embodiments of the invention will be described below in relation to a system and/or a method. Features, advantages or alternative embodiments mentioned in this connection are likewise to be transferred to the other claimed subject matters, and vice versa. In other words, the claims in question (which are directed by way of example toward a system) can also be developed by the features that are described or claimed in connection with a method. The corresponding functional features of the method are formed by corresponding representational modules.

At least one embodiment of the invention is based on the idea of automatically selecting a scanning protocol for the tomographic recording of an X-ray image of a patient in that at least one patient-specific value is retrieved in the internal memory of a first computer, wherein the patient-specific value can in particular be a measure of the anticipated X-ray absorption by the patient, and of automatically comparing this patient-specific value with retrievably stored reference values, wherein one scanning protocol can be associated with each reference value. Finally, according to the invention the scanning protocol is automatically selected by way of the first computer using the comparison.

Automating selection of the scanning protocol simplifies selection since according to an embodiment of the invention no manual selection of the scanning protocol has to be made. At most confirmation of the automatically selected scanning protocol by an operator can also prove to be expedient.

An embodiment of the inventive automatic selection of a suitable scanning protocol also takes place more quickly than a manual selection. The faster selection accelerates the entire workflow of the tomographic recording and makes it more efficient. The patient has to expend less time on the tomographic recording as a result. The accelerated workflow also creates added economic value for the operator of an X-ray tomograph.

An embodiment of the inventive automatic selection of the scanning protocol is also associated with increased reliability because, in contrast to manual selection, automatic selection can be implemented largely without errors. For the patient greater reliability has the fundamental advantage that repeating the tomographic recording and the increased exposure to radiation associated therewith due to an incorrectly selected scanning protocol are less probable. This applies in particular to patients whose significant patient-specific values differ from those of an average patient. This is the case by way of example in the case of weight for obese patients or in the case of weight and age for children.

If the patient-specific value is the weight of the patient, then this can be ascertained particularly easily by way of an examination table, wherein the examination table is designed to detect is the weight of a patient positioned on the examination table.

A high image quality is also ensured by an embodiment of the inventive automatic selection because selection of a disadvantageous scanning protocol is avoided. Overall, an embodiment of the invention consequently brings about improved medical diagnosis.

Automatic selection can also be improved if an embodiment of the inventive method also includes taking an overview image of the patient and the automatic derivation of at least one patient-specific value from the overview image by way automatic image analysis, because many different values, by way of example values relating only to specific regions of the patient, can be derived by automatic image analysis. An overview image of this kind is by way of example a topogram or a photographic image.

According to one aspect of an embodiment of the invention automatic parameterizing of the selected scanning protocol occurs by way of at least one patient-specific value in such a way that the recording of the patient has a predeterminable image quality in the case of a predeterminable dose. The scanning protocol is therefore individually adapted by the parameterizing to the respective patient, whereby image quality and dose efficiency are improved still further.

An embodiment of the invention also includes a computer program product, wherein the computer program product includes a computer program which is stored on a data carrier or a memory of a computer and includes commands which can be read by the computer and which are intended to carry out an embodiment of the method if the commands are executed on the computer. An embodiment of the inventive method can consequently be carried out quickly, reliably and reproducibly.

If an embodiment of the invention is implemented in the form of a system it comprises a first computer which is designed to carry out an embodiment of the inventive method. The patient-specific value can be retrievably stored on a second computer and can be retrieved in the internal memory of the first computer via a network connection.

An embodiment of the invention can also be implemented in the form of an imaging system, comprising an X-ray tomograph.

BRIEF DESCRIPTION OF THE DRAWINGS

The invention will be described and explained in more detail below with reference to the example embodiments illustrated in the figures, in which.

DETAILED DESCRIPTION OF THE EXAMPLE EMBODIMENTS

Figure 1:
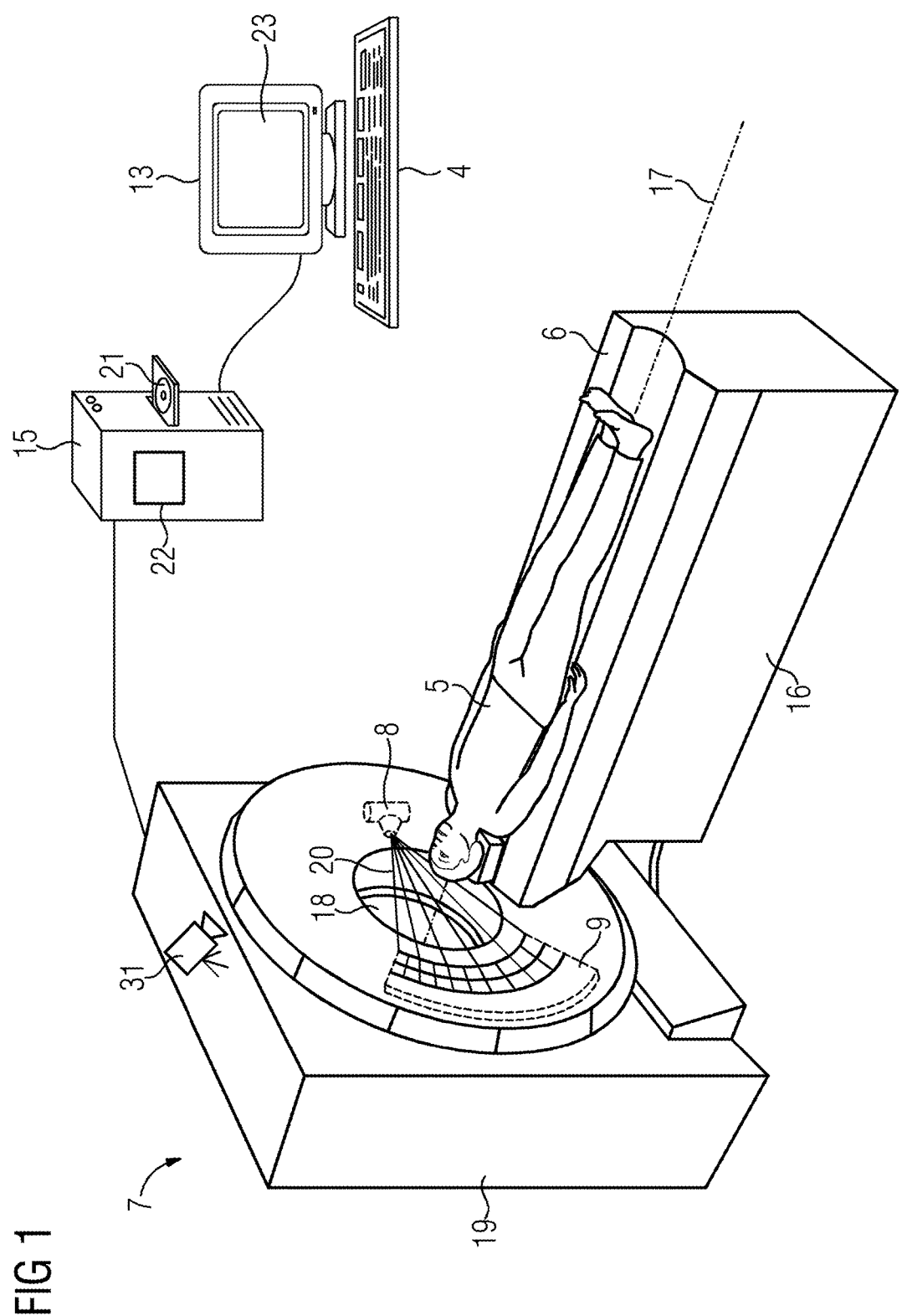
FIG. 1 shows an inventive computed tomography imaging system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an inventive computed tomography imaging system 7.

During the tomographic recording of an X-ray image the patient 5 lies on an examination table 6 which is connected to a table base 16 in such a way that it supports the examination table 6 with the patient 5. During a tomographic recording the examination table 6 moves the patient 5 in a spiral mode along an axis of rotation 17 through the opening 18 in a gantry 19 of the computed tomography imaging system 7. During this movement a large number of projection scans of a body part of the patient 5 are created. During the tomographic recording of an X-ray image the X-ray detector 9 and the X-ray emitter 8, which cooperates with the X-ray detector 9, move about the axis of rotation 17. X-ray emitter 8 and X-ray detector 9 are arranged in the gantry 19 in such a way that they oppose one another and the X-ray beams 20 of the X-ray emitter 8 are detectable by the X-ray detector 9. The X-ray detector 9 of a computed tomography imaging system 7 shown here is a detector with a plurality of rows and columns.

An X-ray detector 9 is conventionally designed as a scintillation counter in which the high-energy X-ray photons are converted by way of a scintillator into low-energy photons in the optical spectrum and then detected by way of a photodiode. Alternatively the X-ray detector 9 can be designed as a directly converting detector which converts the high-energy X-ray photons by way of a semi-conductor material directly into an electrical signal current by internal photo excitation using the photovoltaic principle. The X-ray emitter 8 is conventionally an X-ray tube. In principle other X-ray emitters 8, which are suitable for tomographic imaging, may also be used, however.

In a further embodiment the computed tomography imaging system 7 has two mutually cooperating pairs of X-ray emitters 8 and X-ray detectors 9 respectively, so the computed tomography imaging system 7 is particularly suitable for multiple-energy recordings. In an alternative embodiment (not shown here) the computed tomography imaging system 7 is a C-arm X-ray apparatus. Other X-ray emitters 8 and X-ray detectors 9 in particular can be used in a C-arm X-ray apparatus. A flat detector by way of example can be used as the X-ray detector 9. In addition, the X-ray radiation in the case of a computed tomography imaging system 7 usually has a fan shape, whereas in the case of a C-arm X-ray apparatus it usually spreads conically.

To select the appropriate scanning protocol for a patient 5 the inventive computed tomography imaging system 7 also includes a first computer 15 on which a large number of scanning protocols is retrievably stored, or which can be retrieved from the first computer 15 via a network. According to the invention the first computer 15 is designed for retrieving at least one patient-specific value in its internal memory. According to one aspect of the invention, the at least one patient-specific value is a measure of the anticipated X-ray absorption by the patient 5. The first computer 15 also has an arithmetic logic unit 22, designed for automatic comparison Vg of a patient-specific value with retrievably stored reference values, wherein one scanning protocol can be associated with each reference value, and is also designed for automatic selection As of a scanning protocol by way of the first computer 15 using the automatic comparison Vg.

The first computer 15 is also fitted with an arithmetic logic unit 22, wherein the first computer 15 is designed to load a computer program into its internal memory. The computer program includes commands which can be read by the first computer 15 and is itself part of a computer program product. The computer program product can by way of example be stored on a computer-readable medium 21. The commands, which can be read by the first computer 15, of the computer program are configured to carry out the inventive method if the commands are executed on the first computer 15.

The computer-readable medium 21 can also be by way of example a DVD, USB stick, hard drive or a diskette. The first computer 15 is connected to an output unit 13, by way of example for graphical output of tomographic recordings 23. The output unit 13 can also graphically output an automatically selected scanning protocol, for instance by displaying the title "AbdomenSpiralChild". The output unit 13 is by way of example a (or several) LCD, plasma, or OLED screen(s). The first computer 15 is also connected to an input unit 4. The input unit 4 is used by way of example to actuate an automatically selected scanning protocol by way of a mouse click and thereby start the tomographic recording. The input unit 4 is by way of example a keyboard, mouse, what is known as a touchscreen, or a microphone for speech input.

The system for the automatic selection As of a scanning protocol is designed in such a way that it can carry out the inventive method steps and/or can control devices appropriate to the execution of the inventive method. In particular the patient-specific value can be retrievably stored on a second computer and be retrievable in the internal memory of the first computer 15 via a network connection. The second computer can in particular be a radiology information system, RIS for short, on which a large number of patient-specific data, in particular the age or sex of the patient 5, is often stored.

The arithmetic logic unit 22 can be designed in the form of hardware or software. An interface enables the arithmetic logic unit 22 to communicate with the computed tomography imaging system 7. In the embodiment shown here the arithmetic logic unit 22 or the first computer 15 has further interfaces in order to be able to communicate with the input unit 4 or an output unit 13. The interface is a generally known hardware or software interface, e.g. the PCI bus, USB or Firewire hardware interfaces.

In one embodiment of the invention, the computed tomography imaging system 7 is designed to record an overview image of the patient 5, and for automatic derivation Ab of at least one patient-specific value from the overview image by way of automatic image analysis By. In one variant of this embodiment the overview image is a topogram. In this variant a derived patient-specific value can be the actually measured X-ray absorption of the patient 5, at least in the projection direction of the topogram. The X-ray absorption in another projection direction can also be calculated by the assumption of an elliptical body cross-section. Metal implants which are highly absorbent and which require selection of a particular scanning protocol may also be detected in a topogram. Automatic image analysis By can therefore also include detection of a metal implant.

In a further embodiment the overview image is a photographic image. A photographic image of this kind can be taken by way of example by way of a camera 31 secured to the gantry 19 or integrated in the gantry 19. In this case it can be calculated, without exposure of the patient 5 to X-ray radiation, to what extent the patient 5 absorbs X-ray radiation. For this purpose the contour of the patient 5 is calculated on the basis of the photographic image. By assuming typical soft tissue and bone densities, the anticipated X-ray absorption of the patient 5 in various projection directions can then be calculated from the contour. The weight of the patient 5 can also be estimated solely on the basis of the calculated contour.

Figure 2:
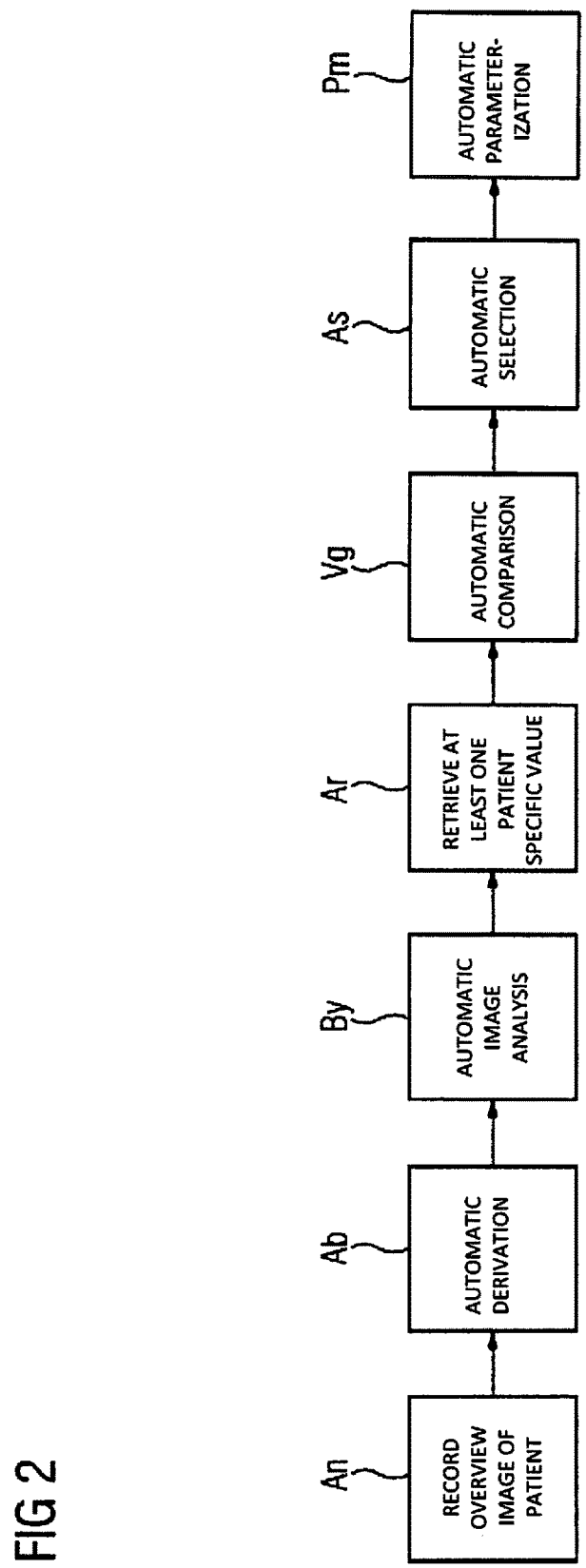
FIG. 2 shows a flow diagram of an embodiment of the inventive method.

FIG. 2 shows a flow diagram of an embodiment of the inventive method.

Automatic image analysis By includes steps of image processing such as segmenting and filtering. Automatic image analysis By can also include detecting specific markers in or on the body of the patient 5, wherein the markers are by way of example a previously selected region of the patient 5, such as a specific organ, or a specific bone structure. The step of automatic derivation Ab of a patient-specific value can also occur by way of automatic image analysis By. For the purpose of automatic derivation Ab, automatic image analysis By can also include the step of pattern recognition in which specific features from the overview image are classified by way of pattern recognition.

By way of example the automatic comparison Vg of a patient-specific value with retrievably stored reference values can occur in such a way that a limit value is set and a specific scanning protocol is to be used when this is exceeded or fallen below. If the patient-specific value is by way of example the weight of a patient 5, a first limit value can be 100 kg and a second limit value 120 kg. The automatic comparison Vg can also include a case differentiation, by way of example by taking into account whether the patient 5 is a male or female person 5. Therefore a first limit value in the case of a female patient 5 can be by way of example 90 kg instead of 100 kg. The step of automatic comparison Vg can therefore include a plurality of comparison steps in accordance with various patient-specific values.

In one embodiment of the invention a patient-specific value is the weight of the patient 5. It is important in particular in the case of heavy or obese patients to select the appropriate parameters for a tomographic recording. In the case of a tomographic recording with a standard protocol for normal-weight patients 5 the applied dose would be too low, so the image quality would be poor and in the worst case the recording would have to be repeated. It may be necessary by way of example with a particularly heavy patient to increase the tube current and simultaneously reduce the feed rate of the examination table 6 along the axis of rotation 17. The automatic selection As of the appropriate scanning protocol according to the invention occurs particularly quickly and reliably. In a further embodiment the weight of a patient 5 positioned on the examination table 6 can in particular be detected directly by scales integrated in the examination table 6.

In one embodiment the patient-specific value is the age of the patient 5, because, due to their smaller size, their, usually, lower body weight and their bone structure that is different from an adult's, children absorb X-ray radiation to a lesser degree than fully grown patients 5. The use of a standard protocol for adults would therefore lead to an unnecessarily high dose rate in children. The inventive automatic selection As of the scanning protocol means that a tomographic recording can take place as quickly and reliably as possible with the appropriate parameters.

In further embodiments the patient-specific value can be based on the measurement of the heartbeat or breathing of the patient 5. The patient-specific value can by way of example be a value for the respiratory rate, the frequency of the heartbeat or another parameter derived from an ECG.

A plurality of patient-specific values may also be retrieved. The retrieved patient-specific values can in particular be derived from an overview image. The automatic comparison Vg is then multidimensional since a plurality of patient-specific values is compared with different sets of reference values. One set of reference values includes by way of example weight values, while a second set of reference values includes the level of X-ray absorption through the abdomen of the patient 5 by way of example. The automatic selection As can occur on the basis of a spacing criterion, wherein the spacing between the patient-specific value or the patient-specific values and the reference values is determined during the comparison step. With an automatic comparison Vg of a plurality of patient-specific values with different sets of reference values the spacings along various dimensions can be weighted, wherein one dimension is given by way of example by "weight" and a further dimension is given by "X-ray absorption through the abdomen" or "respiratory rate". Alternatively the automatic comparison Vg of a plurality of patient-specific values with the reference data can occur in such a way that hierarchical comparisons take place one after another in different dimensions. In this alternative case the automatic comparison Vg includes passing through a decision tree.

Automatic parameterizing Pm of the selected scanning protocol by way of a patient-specific value can also occur in such a way that the tomographic recording of the patient 5 has a predefinable image quality in the case of a predefinable dose. The criterion for a predefinable image quality can in particular be the signal-to-noise ratio, or spatial or temporal resolution. The criterion for the predefinable dose can also be a specific accumulated dose value which can in particular be as low as possible. Automatic parameterizing Pm includes the individual values, which are provided in a specific selected scanning protocol for the parameters of the scanning protocol (such as the intensity of the X-ray radiation), being parameterized. The values for the individual parameters of the scanning protocol are adjusted during automatic parameterizing Pm to the retrieved patient-specific value in each case. The adjustment assumes that a certain value for a specific parameter of the scanning protocol with a specific patient-specific value is regarded as optimal. If a specific scanning protocol has then been automatically selected according to the invention because, using the automatic comparison Vg, a retrieved patient-specific value is closest to a reference value, but the retrieved patient-specific value does not exactly match the reference value, then there can be a further improvement in the selected scanning protocol by way of automatic parameterizing Pm. This ultimately improves the quality of the tomographic recording. Automatic parameterization Pm can also occur by way of a plurality of patient-specific values.

Within the context of the present application "automatic" means that the respective step proceeds independently by way of the first computer 15, and substantially no interaction of the user with the first computer 15 is necessary for the respective step. In other words, the calculations which are behind the steps that are essential to the invention, such as automatic comparison Vg, automatic selection As, etc., are performed by the first computer 15 or by the arithmetic logic unit 22. At most the user has to confirm the results calculated in the individual steps or execute intermediate steps. In further embodiments of the invention, with steps carried out "fully automatically" no interaction of the user with the first computer 15 is necessary at all to carry out these steps that are essential to the invention. Regardless of whether the individual steps are carried out "automatically" or "fully automatically" the inventive method can be part of a workflow which also requires the interaction of a user. The interaction with the user can consist in them manually selecting a category of scanning protocol and/or a clinical question, by way of example from a menu presented by way of the first computer 15. This corresponds to the selection of a category of reference values with the aid of which the automatic comparison Vg is to be made.

Although the invention has been illustrated and described in detail by the preferred example embodiments, it is not limited by the disclosed examples and a person skilled in the art can derive other variations herefrom without departing from the scope of the invention. Method steps can in particular be carried out in a sequence different to the one disclosed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a computer program. The computer program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the computer program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for an automatic selection of a scanning protocol for a tomographic recording of an X-ray image of a patient, the method comprising:

retrieving, by a first computer, at least one patient-specific value from a second computer via a network connection between the first computer and the second computer, the at least one patient-specific value being a measure of an anticipated X-ray absorption of the patient;

storing the at least one patient-specific value in an internal memory of the first computer;

retrieving the at least one patient-specific value from the internal memory of first computer;

automatically comparing the at least one patient-specific value with corresponding retrievably stored reference values, each reference value being associated with a scanning protocol from among a plurality of scanning protocols; and automatically selecting the scanning protocol by way of the first computer using the automatically comparing.

2. The method of claim 1, wherein at least one of the at least one patient-specific value includes an age of the patient.

3. The method of claim 2, wherein the at least one patient-specific value includes at least two patient-specific values, and wherein at least one of the at least two patient-specific value includes a weight of the patient.

4. The method of claim 2, further comprising:
recording an overview image of the patient; and
automatically deriving the at least one patient-specific value from the overview image by way of automatic image analysis.

5. The method of claim 4, wherein the overview image includes a topogram or a photographic image.

6. The method of claim 1, wherein at least one of the at least one patient-specific value includes a weight of the patient.

7. The method of claim 6, further comprising:
recording an overview image of the patient; and
automatically deriving the at least one patient-specific value from the overview image by way of automatic image analysis.

8. The method of claim 7, wherein the overview image includes a topogram or a photographic image.

9. The method of claim 1, further comprising:
recording an overview image of the patient; and
automatically deriving the at least one patient-specific value from the overview image by way of automatic image analysis.

10. The method of claim 9, wherein the overview image includes a topogram or a photographic image.

11. The method of claim 1, further comprising:
automatically parameterizing the selected scanning protocol by use of the at least one patient-specific value in such a way that the tomographic recording of the patient includes a definable image quality in the case of a definable dose.

12. A non-transitory computer-readable storage medium storing a computer program, including commands that, when executed by a computer, cause the computer to carry out the method of claim 1.

13. A system for an automatic selection of a scanning protocol for a tomographic recording of an X-ray image of a patient, the system comprising:
a first computer configured to retrieve at least one patient-specific value from an internal memory of the first computer, the at least one patient-specific value being a measure of anticipated X-ray absorption of the patient; and an arithmetic logic unit configured to automatically compare the at least one patient-specific value with corresponding retrievably stored reference values, each reference value being associated with a respective scanning protocol from among a plurality of scanning protocols, the arithmetic logic unit being further configured to automatically select a scanning protocol, by way of the first computer, using the automatic comparison;

wherein the first computer is further configured to
retrieve the at least one patient-specific value from a second computer via a network connection between the first computer and the second computer, and
store the at least one patient-specific value in the internal memory.

14. An imaging system, comprising:
an X-ray computed tomography system for tomographic recording of an X-ray image of a patient, comprising the system of claim 13.

15. The imaging system of claim 14, further comprising:
an examination table, wherein the examination table is configured to detect a weight of a patient positioned on the examination table, and wherein the at least one patient-specific value includes the weight of the patient.

16. The imaging system of claim 14, wherein the X-ray computed tomography system is configured to
record an overview image of the patient; and
automatically derive the at least one patient-specific value from the overview image by way of automatic image analysis.

\* \* \* \* \*